United States Patent [19]

Cavazza

[11] Patent Number: 5,227,518
[45] Date of Patent: Jul. 13, 1993

[54] L-CARNITINE DERIVATIVES AS THERAPEUTICAL AGENTS FOR TREATING MYOPATHIES AND NEURONAL DEGENERATION AND FOR INHIBITING PROTEOLYSIS

[75] Inventor: Claudio Cavazza, Rome, Italy

[73] Assignee: Sigma-Tau Industrie Farmaceutiche Riunite S.p.A., Rome, Italy

[21] Appl. No.: 890,009

[22] Filed: May 29, 1992

[30] Foreign Application Priority Data

May 29, 1991 [IT] Italy .................. RM91 A000363

[51] Int. Cl.$^5$ .................. C07C 67/02; A61K 31/22
[52] U.S. Cl. .................................................. 560/253
[58] Field of Search ............... 560/253; 514/476, 478, 514/507, 740, 893, 894

[56] References Cited

U.S. PATENT DOCUMENTS

| 4,609,673 | 9/1986 | Eggerer et al. | 560/253 |
| 4,727,151 | 2/1988 | Bodor | 560/253 |
| 4,874,554 | 10/1989 | Lange et al. | 560/253 X |

Primary Examiner—Arthur C. Prescott
Attorney, Agent, or Firm—Oblon, Spivak, McClelland, Maier & Neustadt

[57] ABSTRACT

The use is disclosed of compounds of general formula

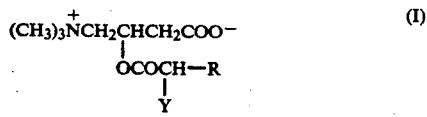

wherein:
Y is hydrogen or methyl and
R is an unsubstituted or substituted alkyl group selected from methyl, ethyl and isopropyl, and the pharmacologically acceptable salts thereof, for treating myopathies, neuronal degeneration and some pathologies affecting the liver, skeletal muscles and myocardium.

The compounds can be administered orally or parenterally.

10 Claims, No Drawings

L-CARNITINE DERIVATIVES AS THERAPEUTICAL AGENTS FOR TREATING MYOPATHIES AND NEURONAL DEGENERATION AND FOR INHIBITING PROTEOLYSIS

The present invention relates to the use of acyl derivatives of L-carnitine of formula (I) and their pharmacologically acceptable salts of formula (I') as therapeutical agents for treating myopathies, neuronal degeneration (as it occurs e.g. in Alzheimer's disease) and for inhibiting the proteolysis of liver, skeletal muscle and myocardium.

The acyl derivatives of L-carnitine according to the invention are represented by the following formula (I)

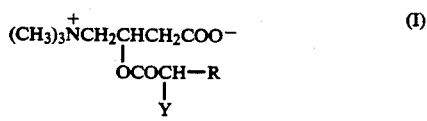

wherein:
Y is hydrogen or methyl, and
R is an unsubstituted or substituted alkyl group selected from methyl, ethyl and isopropyl.

Formula (I) represents the compounds of the present invention as inner salts. Encompassed within the scope of the present invention are also the pharmacologically acceptable salts of the compounds of formula (I) that have formula (I')

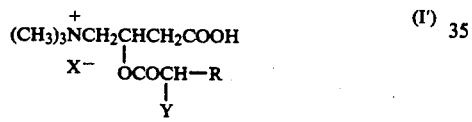

wherein R and Y have the above-identified meanings and $X^-$ is the anion of a pharmacologically acceptable acid selected e.g. from chloride, bromide, orotate, acid aspartate, acid citrate, acid phosphate, acid fumarate, lactate, acid maleate, acid oxalate and acid sulphate.

Among the compounds of formula (I) the following are preferred:

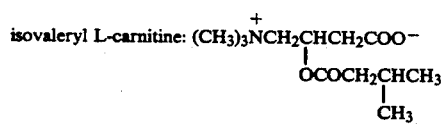

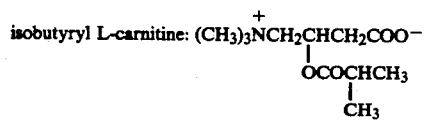

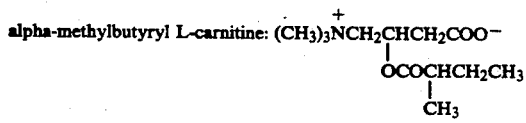

Among the compounds (a)–(c), isovaleryl L-carnitine is particularly preferred.

The compounds of formula (a)–(c) are known compounds.

Isovaleryl L-carnitine is a natural product: it forms by catabolic conversion of L-leucine, one of the essential aminoacids.

Isovaleryl L-carnitine can be synthesized by reacting a solution of L-carnitine chloride in trifluoroacetic acid with isovaleryl chloride at room temperature. Upon termination of the reaction, isovaleryl L-carnitine is precipitated by adding ethyl ether to the reaction mixture (m.p. 173°–175° C.; rotatory optical power-23 (c=1, $H_2O$)).

Also isobutyryl carnitine and alpha-methylbutyryl carnitine are natural products (see e.g. L. L. Bieber e Y. R. Choi, Isolation and identification of aliphatic short-chain acylcarnitines from beef heart: Possible role for carnitine in branched-chain aminoacid metabolism, in Proc. Natl. Acad. Sci USA, 74, n 7, pp 2795–2798, 1977). Methods for synthesizing these acyl derivatives of carnitine are e.g. disclosed by E. Strack and D. Müller, Darstellung von O-acyl-carnitinen, in Hoppe Seyler's Z. Physiol. Chem. 351, pp 95–98, 1970 and by T. Bohmer e J. Bremer, Propionylcarnitine, physiological variations in vivo, in Biochim. Biophys. Acta, 152, pp 559–567, 1968.

Among the pharmacologically acceptable salts of formula (I'), isovaleryl L-carnitine acid fumarate is particularly preferred. Since it is a novel compound, its preparation and physico-chemical characteristics are described hereinbelow.

Preparation of isovaleryl L-carnitine acid fumarate (ST 743)

Isovaleryl L-carnitine inner salt (25 g; 0.11 mole) were dissolved in 500 mL $H_2O$ and fumaric acid (13 g; 0.11 moles) was added to the resulting solution. The solution was lyophilized and the solid product thus obtained was crystallized from isopropanol. 33 g of the title product were obtained.

$[\alpha]_D^{25} = -15.4$ (C=1% $H_2O$)
column: μ Bondapack-$NH_2$ 10 μ
eluant: $CH_3CN$-$KH_2PO_4$ 0.05M (65-35)
flow-rate: 1 mL/min
$R_t = 5.85$ min–13.685 min
Title HPLC: Isovaleryl-L-Carnitine: 67.1% theorical value 67.88%. Fumaric Acid: 31.0% theorical value 32.11%.

Elementary analysis: $C_{16}H_{27}NO_8$:

|  | C % | H % | N % |
|---|---|---|---|
| calc. | 53.18 | 7.53 | 3.88 |
| found | 53.00 | 7.73 | 3.79 |
| $H_2O$ 1% | | | |

TLC:

| $CHCl_3$ | - | IsoprOH | - | MetOH | - | $H_2O$ | - | AcOH |
|---|---|---|---|---|---|---|---|---|
| 4.2 | | 0.7 | | 2.8 | | 1.1 | | 1.1 |

$R_F = 0.5$ ($I_2$) + 0.7 (U.V.)
NMR$D_2O$:

δ 7.2(2H, s, CH=CH); 5.6(1H, m, CH);
                                    |
                                    O 4.0–3.8(2H, m, $N^+CH_2$); 3.2(9H, s, $N^+(CH_3)_3$);

-continued
2.8(2H, d, CH₂COOH); 2.4(2H, m, OCOCH₂);

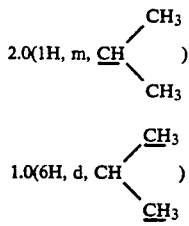

2.0(1H, m, CH(CH₃)(CH₃))

1.0(6H, d, CH(CH₃)(CH₃))

PHARMACOLOGICAL STUDIES

Several pharmacological studies were conducted on the compounds of the present invention.

(A) Studies on Tropic Neuronal activity and Enhancement of Nerve Growth Factor Activity The results of some studies relating to the inherent tropic activity of isovaleryl L-carnitine and the enhancement of the action of nerve growth factor (NGF) on PC 12 cells are hereinbelow described.

One event that is common to the physiology and pathophysiology of the aging process in the central nervous system (CNS), is the reduction of the nerve growth factor (NGF) receptors. NGF is a polypeptide that is essential for the development and maintenance of some classes of neurons.

In the CNS, NGF has trophic effects on the magnocellular cholinergic neurons of the basal forebrain and septum. NGF is released by target tissues of cholinergic innervation, such as hippocampus and front cortex, where it binds to the nerve growth factor receptors (NGFR) on cholinergic terminals and is retrogradely transported to the cell soma in the basal forebrain and septum.

The continuos NGF supply warrants neuron survival.

The finding that NGF exerts neurotrophic activity in CNS has led to the hypothesis that the reported loss of NGFR in senescence with the resulting reduction of NGFR activity is responsible for neuronal cell death and atrophy. Consequently, the therapeutic use of NGF for the treatment of neurological diseases associated with aging has been proposed. However, since the problems associated with NGF absorbence, transport and stability have not been solved, NGF actual therapeutical utilization meets with serious difficulties.

It is known that the treatment of rats with acetyl L-carnitine, ALCAR ®, a naturally occurring substance involved in mitochondrial metabolism of fatty acids prevents certain CNS impairments in aged rats. ALCAR ® treatment of senescent rats prevents the loss of glucocorticoid receptors in the hippocampus and improves the behavioural performances that are related to the limbic system.

ALCAR ® partially prevents the loss of NGFR that occurs in the hippocampus and the basal forebrain of aged rodents.

ALCAR ® has been shown to stimulate NGFR synthesis and enhance the action of NGF on PC 12 cells.

The rat pheochromocytoma (PC 12) cell line was chosen as an in vitro model system for NGF-responsive neurons. PC 12 cells are a cell line derived from a tumor of rat adrenal medulla that display NGFR similar to those described for sympathetic and sensory neurons. PC 12 typically respond to NGF by elongating neurites and developing into electrically excitable cells featuring some characteristics of the post-mitotic cholinergic neuronal phenotype.

The study reported hereinbelow shows that the action of NGF on PC 12 cells is enhanced by isovaleryl carnitine treatment more potently than by ALCAR ® treatment. Thus, isovaleryl carnitine is shown to prevent some degenerative processes in the aged brain by lowering the response threshold of susceptible neurons to neurotrophic factors.

Even more importantly, this study shows that isovaleryl carnitine possesses inherent tropic activity and is per se effective in stimulating neurite outgrowth, even in the absence of NGF.

Rat pheochromocytoma (PC 12) cells were grown in RPMI 1640, supplemented with 5% heat inactivated horse serum +5% heat inactivated fetal calf serum at 37° C. in humidified incubator with 5% $CO_2$ atmosphere and fed on alternate days. At subconfluency, cells were dislodged by vigorous shaking and reseeded at 1:1 ratio. Acetyl L-carnitine, ALCAR ®, and isovaleryl L-carnitine were dissolved in RPMI and added to the cells at the final concentrations indicated in the various experiments.

NEURITE OUTGROWTH EXPERIMENT

PC 12 cells were plated out into 35 mm Petri dishes at a density $2 \times 10^5$ cells/ml. On the sixth day of either ALCAR ® or isovaleryl L-carnitine treatment (1 mM), the cells were added with NGF dissolved in RPMI 1640 at a suboptimal concentration (i.e. ineffective to stimulate neurite outgrowth) of 1 ng/mL (0.037 nM). On day 5 after NGF addition, 100-120 cells from 5-12 randomly chosen microscope fields were counted and assayed for presence of neurites. All the counts were done independently by two investigators on coded samples. After all counts were carried out, codes were broken and the average of the two counts taken as final value estimation. The results are shown in table 1.

TABLE 1

EFFECT OF ISOVALERYL L-CARNITINE (1 mM) ON THE NEURITE OUTGROWTH OF CELLS IN THE PRESENCE OR ABSENCE OR A SUBOPTIMAL NGF DOSE (1 ng/mL).
NEURITIC OUTGROWTH

| | | |
|---|---|---|
| Control | — | no neurites present |
| control + NGF | —/+ | occasional neuritic outgrowth |
| IVC | ++ | neurites present |
| IVC + NGF | +++ | abundant neuritic outgrowth |
| ACETYL L-CARNITINE | — | no neurites present |
| ACETYL L-CARNITINE + NGF | ++ | neurites present |

EFFECT OF ALCAR and ST 857 ON CHOLINE ACETYLTRANSFERASE (ChAT)

The method described by Fonnum, F. in "A rapid radiochemical method for the determination of choline acetyltransferase", J. of Neurochem. (1975) vol. 24, 407:409 was used. Briefly, the compounds were added to the culture medium at final concentration of 1 mM.

The cells were grown for 6 days in the presence of isovaleryl L-carnitine. The medium was changed every other day. On the sixth day the cells were harvested and resuspended directly in a homogenization buffer for ChAT activity assay. Protein content was assayed on an aliquot of the cell suspensions. The results are shown in table 2.

TABLE 2

EFFECT OF ISOVALERYL L-CARNITINE (IVC) (1 mM) ON THE ACTIVITY OF ENZYME CHOLINEACETYLTRANSFERASE (ChAT) IN PC 12 CELLS IN THE PRESENCE OR ABSENCE OF NGF (10 ng/mL).

|  | ChAT nmoli ACh/mg/hour (in the presence of NGF) | ChAT nmoli ACh/mg/hour (in the absence of NGF) |
|---|---|---|
| CONTROL | 50.0 ± 5.2 | 15.7 ± 2.3 |
| IVC | 130.0 ± 6.8 | 48.7 ± 2.6 |
| ACETYL L-CARNITINE | 133.3 ± 4.4 | 33.3 ± 4.2 |

(B) Studies on Proteolysis Inhibiting Activity

Cellular proteins undergo a varyingly rapid turnover (synthesis-degradation) depending on protein constitution, type of tissue containing them and metabolic conditions. Responsible for protein hydrolysis (proteolysis) are various proteases (lysosomal and cytoplasmic proteases) capable of hydrolysing proteins down to all their constituent aminoacids (overall hydrolysis) or to fragments (polypeptides) having more or less large sizes.

These proteases, localized in lysosomes, can digest cytoplasm proteins following sequestration of cytoplasm fragments into lysosomes (macroautophagy). Liver perfusion in aminoacids absence elicits a massive macroautophagic response with attendant fast and complete hydrolysis of cellular proteins.

It was already known that addition to the perfusion medium of the same amount of aminoacids as present in blood inhibits proteolysis. It was also known that addition of leucine only to the perfusion medium brings about 60% of proteolysis inhibition as that induced by all aminoacids.

However, leucine administration cannot be relied on with a view to achieving therapeutical results, because in vivo administration of one single amino acid elicits the release of the other amino acids from tissue proteins so as to restore the necessary nutritional balance.

It was surprisingly found that carnitine derivatives of formula (I) and (I'), and particularly isovaleryl L-carnitine, antagonize liver proteolysis without bringing about the harmful effect induced by leucine administration.

Furthermore, it was found that the compounds of formula (I) and (I') are effective in liver regeneration and healing of liver tissue following experimentally-induced lesions.

In order to assess the inhibiting efficacy on liver proteolysis, the following experimental model was used.

Male Wistar rats weighing 130-140 g maintained on standard laboratory chow and water ad libitum were used in the perfusion experiments. The animals were anaesthetizied by intraperitoneal injection of ketamine (16 mg/100 g) and heparinized (1000 U).

Livers were perfused by the in situ technique described by Mortimore and Poso, Multiphasic control of hepatic protein degradation by regulatory amino acids, *Journal of Biological Chemistry* 262:16322–16327 (1987). Perfusion was started in the single pass mode (not recirculating) and continued for 40 minutes. At the end of the single pass phase, the perfusate was fed to a cyclic perfusion reservoir containing 50 mL of perfusion medium and 18 μM of cycloheximide.

Following 30 seconds of wash-out, the medium was recirculated for 15 minutes. All tests were performed at a flow-rate of 11 mL/min., at 37° C.

The perfusion medium consisted of Krebs-Ringer bicarbonate buffer with 4.0% (p/v) of bovine plasma albumine (Fraction V, Sigma Chemical) and 10 mM glucose gassed with $O_2/CO_2$ 95/5% (v/v).

Following addition of the compounds under examination, the buffer solution was filtered through a 0.45 μs MILLIPORE filter and pH adjusted to 7.4 in the presence of $O_2/CO_2$ 95/5%.

Proteolysis was assessed from the release rate of valine in the cyclic perfusion liquid in the presence of cycloheximide according to the method described by Khairallah and Mortimore, J. Biol. Chem. 251, 1375–1384 (1976).

Using this model, liver proteolysis rates were studied in the presence e.g. of isovaleryl L-carnitine acid fumarate (ST 743) and an equimolar amount of L-leucine. It was found that the former inhibits proteolysis more potently than the latter throughout the range of tested concentrations.

It was also shown that proteolysis inhibition is dose-dependant.

The effect of ST 743 on proteolysis inhibition assuming valine release (nmoles/mL perfusate/mg liver) as marker of proteolysis is shown in the following table 3 (in parentheses the number of animals).

TABLE 3

| GROUPS | VALINE |
|---|---|
| UNTREATED x̄ ± S.E. (8) | 17.74 ± 1.286 |
| ST 743 _ 0.22 mM x̄ ± S.E. (7) | 22.32 ± 2.165 (+25.8%) |
| ST 743 _ 0.44 mM x̄ ± S.E. (8) | 14.46 ± 2.173 (−18.5%) |
| ST 743 _ 0.88 mM x̄ ± S.E. (8) | 8.71 ± 0.959▲ (50.9%) |

Student's "t" test: ▲ (p ≤ 0.001)

(C) D-galactosamine-induced intoxication

As known, D-galactosamine administered to laboratory animals produces pathological alterations similar to human viral hepatitis.

Male Wistar rats, weighing 200–250 grams after having been caged on a 12-hour light and dark cycle for about one week were used. Food and water were freely available. The rats were kept fasting for 18 hours before the test started.

Following the conditioning, the animals were divided in groups, taking care to collect animals having substantially identical body weights in the same group.

In order to induce liver damage, 500 mg/kg body weight of D-galactosamine dissolved in 0.9% saline (pH=7.4) were administered i.p. in 5 mL/kg body weight.

1 hour and 8 hours following hepatotoxicant administration, one group of animals was orally administered isovaleryl L-carnitine chloride (ST 551) and a further group isovaleryl L-carnitine acid fumarate (ST 743).

Blood samples were drawn 24 and 28 hours following hepatotoxicant administration.

Blood was centrifuged (3.000 rpm) and on the serum thus obtained transaminases (SGOT, SGPT), glycemia and urea were assayed.

These parameters are suitable for assessing the intoxication level induced in laboratory animals since a typical symptom of liver damage is the appearance of increased enzyme activity in serum.

The data are statistically significant (p<0.05). Glycemia and urea were not modified. The test results are shown in table 4.

TABLE 4

GALACTOSAMINE (500 mg/5 ml/kg i.p.) INDUCED INTOXICATION
Treatment:
treated with ST 551 (Isovaleryl L-carnitine chloride) 100 mg/kg/10 ml × OS twice
treated with ST 743 (Isovaleryl acid L-carnitine fumarate 100 mg/kg/10 ml × OS twice
(eq. Mol. to ST 551)

| | 24 hours following galactosamine administration | | 28 hours following galactosamine administration | |
|---|---|---|---|---|
| | SGOT U/l | SGPT U/l | SGOT U/l | SGPT U/l |
| UNTREATED | 281.2 ± 14.82 (6) | 59.5 ± 14.64 (6) | 220.62 ± 13.9 (6) | 53.00 ± 5.43△ (5) |
| CONTROL | 1131.7 ± 227.3 (4) | 494.0 ± 102.6 (4) | 1142.0 ± 222.8 (5) | 720.8 ± 177.6 (5) |
| TREATED WITH ST 551 | 808.6 ± 692. (6) | 347.3 ± 38.6 (6) | 833.18 ± 236.2 (4) | 356.0 ± 124.8 (4) |
| TREATED WITH ST 743 | 801.59 ± 48.3 (6) | 352.8 ± 44.4 (5) | 579.90 ± 76.01 (5) | 252.8 ± 59.32 (5) |

Student's "t" test: , △ and  indicate P < 0.05, P < 0.01 and P < 0.001, respectively. In parenthesis the number of animals

D

Finally, the compounds of formula (I) and (I'), particularly isovaleryl L-carnitine acid fumarate, were shown to be active in a model of carbon tetrachloride-induced hepatic cirrhosis. The model was based on the method described by E. Proctor and K. Chatamra in High yield micromodular cirrhosis in the rat, Gastroenterology 83, 1183–90 (1982).

The compounds of the present invention are orally or parenterally administered, in any of the usual pharmaceutical forms which are prepared via the conventional procedures well-known to those persons skilled in pharmaceutical technology. These forms include solid and liquid oral unit dosage forms such as tablets, capsules solutions, syrups and the like as well as injectable forms, such as sterile solutions for ampoules and phials.

For these pharmaceutical forms the usual solvents, diluents and excipients are used. Optionally, sweetening, flavouring and preservative agents can also be present. Non limiting examples of such agents are sodium carboxymethylcellulose, polysorbate, mannitol, sorbitol, starch, avicel, talcum and other agents which will be apparent to those skilled in the pharmaceutical technology.

The dose which is administered will be determined by the attending physician having regard to the age, weight and general conditions of the patient, utilizing sound professional judgement. Although effective results can be noticed at doses as low as 5 to 8 mg/kg of body weight daily, a dose of from about 10 to 50 mg/kg of body weight is preferred. Whenever necessary, larger doses can be safely administered in view of the low toxicity of the compounds of this invention.

Therefore, pharmaceutical compositions in unit dosage form comprise from about 50 to about 500 mg of a compound of formula (I) or an equivalent amount of a pharmacologically acceptable salt thereof of formula (I').

I claim:
1. Use of an acyl derivative of L-carnitine, having general formula (I)

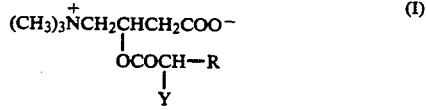

wherein:
Y is hydrogen or methyl and
R is an unsubstituted or substituted alkyl group selected from methyl, ethyl, and isopropyl
or a pharmacologically acceptable salt thereof as therapeutical agent for treating myopathies, neuronal degeneration and for inhibiting proteolysis of liver, skeletal muscle and myocardium.

2. The use of claim 1, wherein the pharmacologically acceptable salt has formula (I')

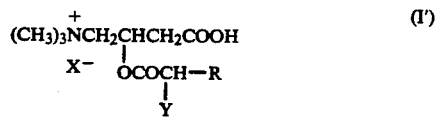

wherein X⁻ is the anion of a pharmacologically acceptable acid selected from chloride, bromide, orotate, acid aspartate, acid citrate, acid phosphate, acid fumarate, lactate, acid maleate, acid citrate, acid phosphate, acid fumarate, lactate, acid maleate, acid oxalate and acid sulphate, and R and Y have the previously defined meanings.

3. Use of an acyl derivative of L-carnitine of formula (I) or (I') for producing a medicament for the therapeutical treatment of myopathies, neuronal degeneration, hepatopathies induced by liver proteolysis, and skeletal muscle and myocardium proteolysis.

4. An orally or parenterally administrable pharmaceutical composition comprising isovaleryl L-carnitine or a pharmacologically acceptable salt thereof as active principle, and a pharmacologically acceptable excipient therefor.

5. An orally or parenterally administrable pharmaceutical composition for the therapeutical treatment of myopathies, neuronal degeneration, hepatopathies featured by liver proteolysis, skeletal muscle and myocardium proteolysis comprising a compound of general formula (I) or (I') as active principle, and a pharmacologically acceptable excipient therefor.

6. The composition of claim 5 comprising as active principle a compound selected from isovaleryl L-carnitine, isobutyryl L-carnitine and alpha-methylbutyryl L-carnitine.

7. The composition of claim 5 in unit dosage form comprising between about 50 and about 500 mg of a compound of general formula (I) or an equivalent amount of a pharmacologically acceptable salt thereof of formula (I').

8. Isovaleryl L-carnitine acid fumarate.

9. The composition of claims 4 or 5, comprising isovaleryl L-carnitine acid fumarate as active ingredient.

10. The composition of claim 7, comprising isovaleryl L-carnitine acid fumarate as active ingredient.

* * * * *